US007927887B2

(12) United States Patent
Choi et al.

(10) Patent No.: US 7,927,887 B2
(45) Date of Patent: Apr. 19, 2011

(54) METHOD OF FABRICATING A DIELECTRIC-MODULATED FIELD EFFECT TRANSISTOR COMPRISING A BIOMOLECULES LAYER FORMED IN A SPACE WHERE A SACRIFICIAL LAYER HAS BEEN REMOVED

(75) Inventors: Yang-Kyu Choi, Daejeon (KR); Hyungsoon Im, Daejeon (KR); Bonsang Gu, Daejeon (KR)

(73) Assignee: Korea Advanced Institute Of Science And Technology (KR)

( * ) Notice: Subject to any disclaimer, the term of this patent is extended or adjusted under 35 U.S.C. 154(b) by 408 days.

(21) Appl. No.: 12/014,380

(22) Filed: Jan. 15, 2008

(65) Prior Publication Data

US 2008/0283939 A1      Nov. 20, 2008

(30) Foreign Application Priority Data

Jan. 15, 2007   (KR) .................. 10-2007-0004292
Sep. 21, 2007   (KR) .................. 10-2007-0096674

(51) Int. Cl.
  *H01L 51/46*      (2006.01)
(52) U.S. Cl. ............................. 438/1; 438/49; 257/409
(58) Field of Classification Search ............... 438/1, 49; 257/E21.409
See application file for complete search history.

(56) References Cited

U.S. PATENT DOCUMENTS

| | | | | |
|---|---|---|---|---|
| 4,411,741 A * | 10/1983 | Janata | ............................ | 257/253 |
| 5,576,563 A * | 11/1996 | Chung | ............................ | 257/253 |
| 5,693,545 A * | 12/1997 | Chung et al. | .................... | 438/49 |
| 7,309,621 B2 * | 12/2007 | Conley et al. | .................... | 438/99 |
| 2005/0053524 A1 * | 3/2005 | Keersmaecker et al. | ....... | 422/88 |
| 2005/0260423 A1 * | 11/2005 | Natesan | ....................... | 428/447 |
| 2006/0154400 A1 * | 7/2006 | Choi et al. | ..................... | 438/49 |
| 2007/0141763 A1 * | 6/2007 | Choi et al. | ..................... | 438/151 |
| 2008/0193705 A1 * | 8/2008 | Kim et al. | ..................... | 428/98 |
| 2008/0193965 A1 * | 8/2008 | Zeng et al. | ..................... | 435/30 |

FOREIGN PATENT DOCUMENTS

KR     10-2006-0086235     7/2006

\* cited by examiner

*Primary Examiner* — Anh D Mai
(74) *Attorney, Agent, or Firm* — The Belles Group, P.C.

(57) ABSTRACT

The present invention relates to a Field-Effect Transistor (FET) and, more particularly, to a Dielectric-Modulated Field-Effect Transistor (DMFET) and a method of fabricating the same. A DMFET according to an embodiment of the present invention comprises a substrate in which a source and a drain are formed, wherein the source and the drain are spaced apart from each other, a gate formed on a region between the source and the drain, of the substrate, wherein at least part of the gate is spaced apart from the substrate, biomolecules formed below a region spaced apart from the substrate, of the gate, and a linker for combining the gate and the biomolecules.

13 Claims, 8 Drawing Sheets

(a)

(b)

(c)

METHOD OF FABRICATING A DIELECTRIC-MODULATED FIELD EFFECT TRANSISTOR COMPRISING A BIOMOLECULES LAYER FORMED IN A SPACE WHERE A SACRIFICIAL LAYER HAS BEEN REMOVED

This Nonprovisional application claims priority under 35 U.S.C. § 119(a) on Patent Application No 10-2007-0096674 filed in Korea on Sep. 21, 2007 and Patent Application No 10-2007-0004292 filed in Korea on Jan. 15, 2007, the entire contents of which are hereby incorporated by reference.

BACKGROUND OF THE INVENTION

1. Field of the Invention

The present invention relates to a Field-Effect Transistor (FET) and, more particularly, to a Dielectric-Modulated Field-Effect Transistor (DMFET) and a method of fabricating the same.

2. Description of the Related Art

As the size of semiconductor devices shrinks, several physical limitations are encountered. A reduction in the device size has reached its limit due to the technical problems of lithography used in the semiconductor process (the wavelength of a light source, scattering of light, NA limit of the lens, the absence of a photoresist, and so on). Further, in the conventional semiconductor devices, an insulating layer was generally made of silicon-oxide ($SiO_2$). However, as the size of a device shrinks, physical limitations, such as breakdown and tunneling, have appeared. To overcome such physical limitations, active research has been done into devices having a novel structure. Of the devices, a molecule device has been proposed. The molecule device is a new concept of a device employing molecules as channels.

The molecule device can be used as a biosensor. The biosensor functions to detect specific molecules, such as enzyme or antibody, which constitute an organism. A method of detecting specific molecules comprises chemical, optical, and electrical methods. Of the methods, the electrical detection method can be used when the quantity of detection target samples is small, and is advantageous in that it has rapid detection. In the electrical detection method, a nano-gap is formed in an existing electrical device, a solution comprising a biomaterial is injected into the nano-gap, and specific materials are detected based on a variation in the electrical property of the device. Thus, the biomaterial formed in the nano-gap serves as an electrical sensor. As the size of a nano-gap reduces, sensitivity is increased and therefore a biomaterial can be detected more effectively.

To fabricate a structure having a nano-size width using the conventional silicon process is inefficient because of several steps of lithography processes, the alignment of a critical value, expensive equipment, environmental limitations of pressure or temperature, a long-time process, and so on. In order to overcome the limitations, a method of employing a breaking phenomenon of a metal nanowire, a method of forming a large-sized gap and reducing the gap size through an electrochemical deposition method, a method of employing ion beam etching, scanning probe lithography, etc., and so on have been introduced. However, the methods or an overall process thereof are problematic in that they are complicated, and have a limit to the formation of a nano-gap with high reproducibility, a low integration level, and a low sensitivity of a sensor.

SUMMARY OF THE INVENTION

Accordingly, the present invention is directed to provide a DMFET having a novel structure of a nano-gap with a high reproducibility, and a method of fabricating the same.

Further, the present invention is directed to provide a DMFET with a high integration level and an improved sensitivity in detecting biomaterials, and a method of fabricating the same.

A DMFET according to an embodiment of the present invention comprises a substrate in which a source and a drain are formed, the source and the drain being spaced apart from each other, a dielectric layer formed on a region between the source and the drain of the substrate and comprising biomolecules, and a gate formed on the dielectric layer.

The gate may be made of metal or polysilicon.

A method of fabricating a DMFET according to an embodiment of the present invention comprises the steps of (a) forming a sacrificial layer on a substrate, (b) forming a gate layer on the substrate and the sacrificial layer, (c) removing the sacrificial layer, and (d) forming a dielectric layer, comprising biomolecules, in a portion from which the sacrificial layer has been removed.

The method may further comprise the step of pattering the gate layer between the step (b) and the step (c).

The sacrificial layer may comprise one or more materials of metal oxide such as silicon oxide, $Al_2O_3$ or $HfO_2$, metal such as Cr, Ti or Al, an organic layer such as a Self-Assembled Monolayer (SAM), and a photoresist.

In the step (d), the dielectric layer may be formed using a SAM or a dehydration and condensation reaction.

A DMFET according to another embodiment of the present invention comprises a wafer, a source and a drain formed on the wafer, the source and the drain being spaced apart from each other, a channel portion connecting the source and the drain, gates formed on the wafer and spaced apart from the channel portion, and a dielectric material formed between the channel portion and the gates and comprising biomolecules.

The gates may be two in number and are opposite to each other on the basis of the channel portion.

A method of fabricating a DMFET according to still another embodiment of the present invention comprises the steps of (a) sequentially forming a substrate and a first insulating layer on a wafer, (b) patterning a second insulating layer on a region in which a gate and a channel portion will be formed in the first insulating layer, (c) growing the first insulating layer by further forming a constituent material of the first insulating layer on the first insulating layer using a thermal oxidization method, (d) etching the first and second insulating layers until the substrate is exposed, (e) forming the gate and the channel portion by implanting an impurity into the exposed region of the substrate, (f) etching the first insulating layer, and (g) forming a dielectric layer comprising biomolecules between the gate and the channel portion.

The first insulating layer may comprise silicon-oxide, and the second insulating layer may comprise silicon-nitride.

In the step (g), the dielectric layer may be formed using a SAM or a dehydration and condensation reaction.

The biomolecules may comprise one of DNA, RNA, protein, ligand, an antibody-antigen material, and enzyme.

A DMFET according to further still another embodiment of the present invention comprises a substrate in which a source and a drain are formed, the source and the drain being spaced apart from each other, a gate formed on a region between the source and the drain, of the substrate, at least part of the gate being spaced apart from the substrate, and biomolecules formed below a region spaced apart from the substrate, of the gate.

A DMFET according to further still another embodiment of the present invention comprises a wafer, a source, a channel portion, and a drain formed in series on the wafer, a gate formed on the other side except for the source side and the drain side of the channel portion on the wafer, the gate being spaced apart from the channel portion, and biomolecules formed between the channel portion and the gate.

A DMFET according to further still another embodiment of the present invention comprises a source, a channel portion, and a drain formed in series on a wafer, a gate formed over the channel portion, at least part of the gate being spaced apart from the channel portion, and biomolecules formed below a region spaced apart from the channel portion, of the gate.

The DMFET may further comprise an insulating layer formed on the channel portion, and a sacrificial layer formed between the insulating layer and the gate. The biomolecules may be formed below the gate, which is exposed by etching both ends of the metal layer.

The DMFET may further comprise a linker between the gate and the biomolecules.

The biomolecules may comprise one of DNA, RNA, nucleotide analogs, protein, peptide, amino acid, ligand, an antibody-antigen material, a sugar structure, an organic/inorganic compound, vitamin, drug, and enzyme.

DETAILED DESCRIPTION OF PREFERRED EMBODIMENTS

Figure 1:
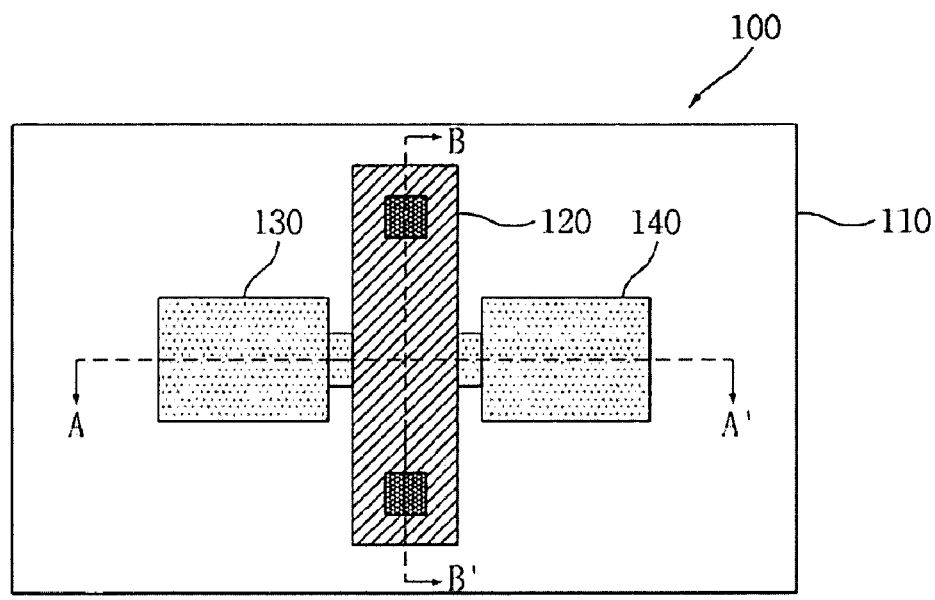
FIG. 1 is a view illustrating a DMFET according to an embodiment of the present invention.
Figure 1:
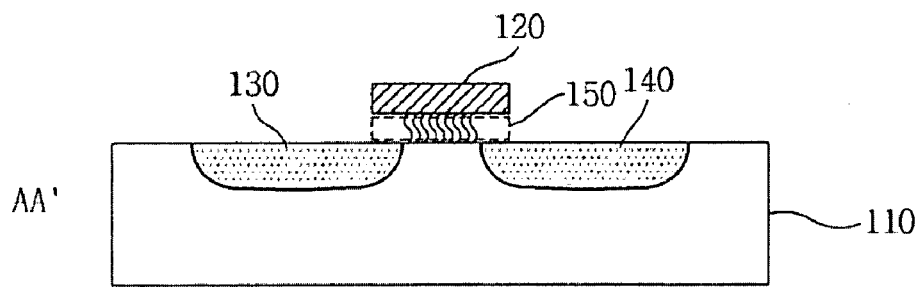
Figure 1:
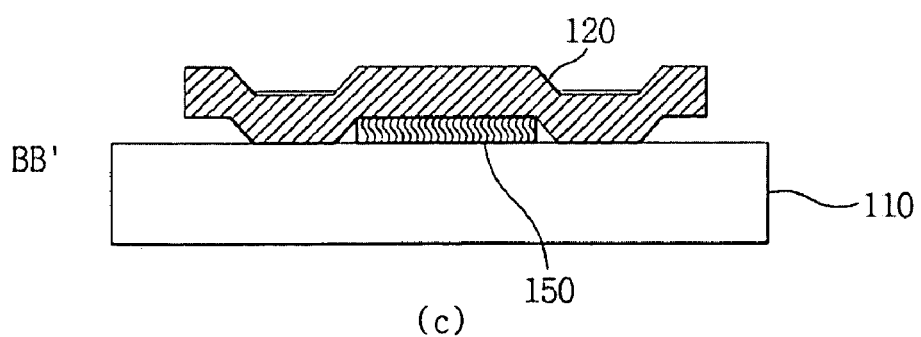

A DMFET and a method of fabricating the same according to the present invention will now be described in detail in connection with specific embodiments with reference to the accompanying drawings. In order to facilitate description, same reference numerals are used in different figures to denote similar elements.

In FIG. 1, (a) is a plan view schematically showing a DMFET 100 according to an embodiment of the present invention, (b) is a sectional view of the DMFET taken along line A-A' in (a), and (c) is a sectional view of the DMFET taken along line B-B' in (a).

As shown in FIG. 1(a), the DMFET 100 comprises a substrate 110, a gate 120, a source 130, and a drain 140. The substrate 110 may comprise a silicon substrate, but not limited thereto. The source 130 and the drain 140 are formed by doping a n-type or p-type impurity into the substrate 110. At this time, it is to be understood that a specific implantation dose and energy can be selected depending on the requirements of a specific end device.

As shown in FIG. 1(b), the source 130 and the drain 140 are formed in the substrate 110, a dielectric layer 150 is formed on a region between the source 130 and the drain 140 of the substrate 110, and the gate 120 is formed on the dielectric layer 150. The dielectric layer 150 refers to a region between the gate 120 and the substrate 110, comprising an air gap, biomolecules, a linker for fixing biomolecules to the substrate 110 or the gate 120 or the like. An overall dielectric constant of the dielectric layer 150 can be decided depending on the dielectric constant of an air gap, biomolecules or a linker itself, whether biomolecules are combined with external detection target materials, the dielectric constant of combined detection target materials and/or the like. Hereinafter, biomolecules constituting the dielectric layer 150 are referred to as receptor biomolecules, and external materials combined with the receptor biomolecules are referred to as detection target materials.

The receptor biomolecules may be DNA, RNA, nucleotide analogs, protein, peptide, amino acid, ligand, antibody-antigen material, a sugar structure, an organic/inorganic compound, vitamin, drugs, enzyme or the like, but may be properly selected according to target materials to be detected. The receptor biomolecules can be fixed to the gate 120 or the substrate 110 using a linker. An example of the linker may comprise a Self-Assembled Monolayer (SAM). When the gate 120 is made of gold (Au), the linker can be formed using a thiol SAM. When the gate 120 is made of silicon, the linker can be formed using a silane SAM. Further, when the receptor biomolecules themselves are material that can be easily fixed to the gate, the linker may not be comprised. In this case, it may be considered that the biomolecules themselves comprise the linker. The thickness of the dielectric layer 150 is a nano-size. The nano-size refers to a thickness range of approximately 10 to 1000 angstrom. This thickness can be controlled easily in the fabrication method of the DMFET according to the present invention, which is described later on.

As shown in FIG. 1(c), the receptor biomolecules are fixed to the dielectric layer 150 between the substrate 110 and the gate 120. At this time, in order to form a nano-gap in which the dielectric layer 150 can be formed, the gate 120 may have a shape in which it is coupled to the substrate 110 on both sides of the region in which the dielectric layer 150 is formed. The nano-gap formed due to this shape of the gate 120 has both sides opened, so a material to be formed in the dielectric layer 150 can be introduced easily into the nano-gap. However, if one end of the gate 120 is coupled to the substrate 110 and therefore can support the gate 120, the shape of the gate layer 120 is not limited. The gate 120 may be made of, preferably, metal or polysilicon. The metal may preferably comprise gold (Au), but not limited thereto. For example, the gate 120 may be made of a material, which can be used to form a gate in a typical MOSFET.

The above-described DMFET can have a reduced size because the dielectric layer 150 comprises the biomaterial when compared with a conventional biosensor device in which the dielectric layer and the biomaterial are separately formed. In addition, since the biomaterial is directly comprised in the dielectric layer, the electrical property of the device according to detection target materials is directly changed. Accordingly, sensitivity to a variation in the electrical property of the device according to a variation of the biomaterial is increased, enabling further improved detection of the biomaterial.

Figure 2:
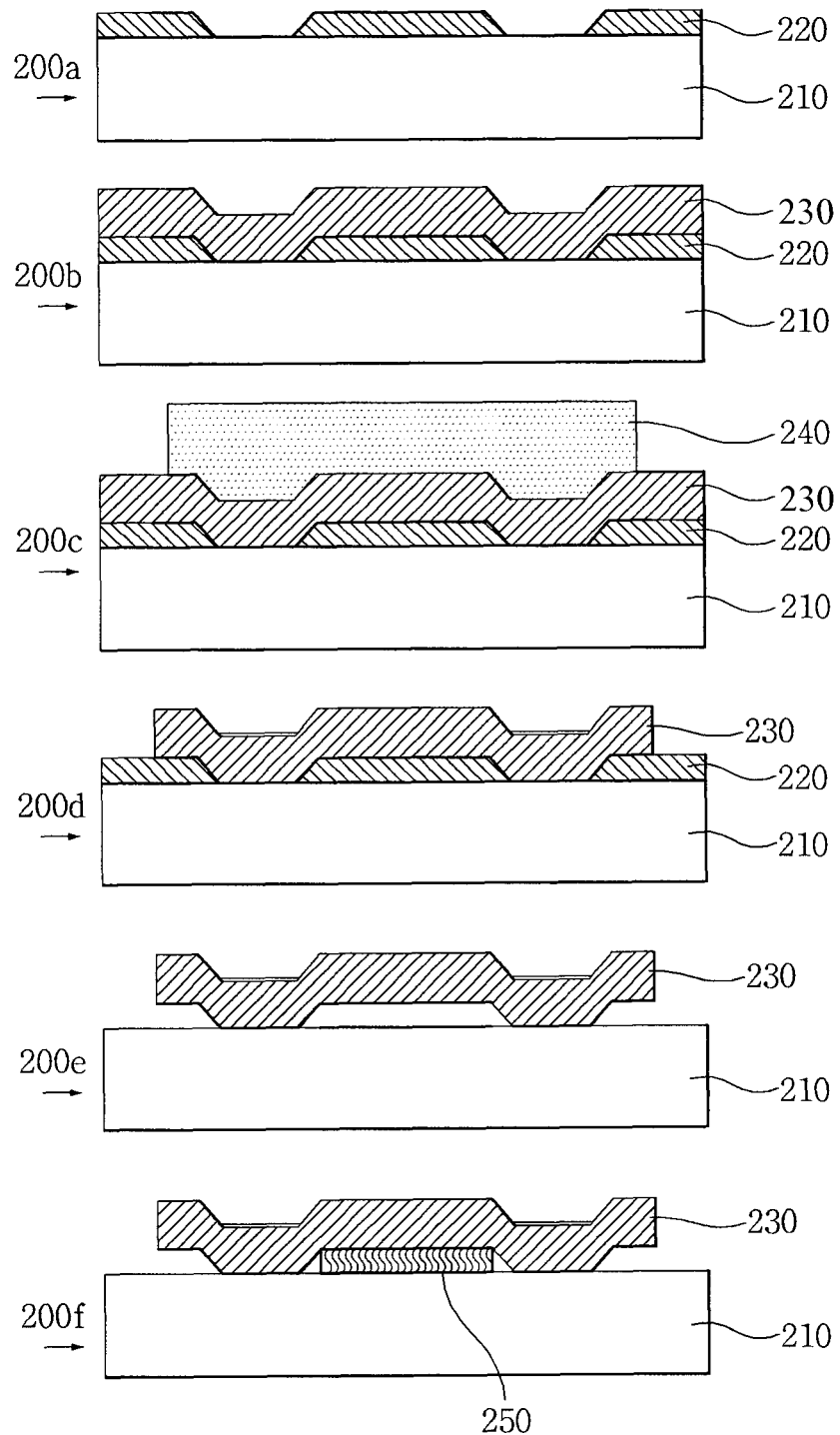
FIG. 2 is a sectional view sequentially illustrating a method of fabricating the DMFET according to an embodiment of the present invention.

FIG. 2 is a sectional view sequentially illustrating a method of fabricating the DMFET according to an embodiment of the present invention.

The source 130 and the drain 140 (not shown) are formed in a substrate 210 using a Local Oxidation of Silicon (LOCOS) or Shallow Trench Isolation (STI) process.

Referring to 200a of FIG. 2, a sacrificial layer 220 is formed on the substrate 210. The sacrificial layer may be formed from one material of metal oxide such as silicon oxide, $Al_2O_3$ or $HfO_2$, metal such as Cr, Ti or Al, an organic layer such as SAM, and a photoresist. The thickness of the sacrificial layer 220 becomes the thickness of a nano-gap of the DMFET later on and may be a nano-size. The nano-size may refer to a range of approximately 10 to 1000 angstrom. In order to pattern the sacrificial layer 220, the sacrificial layer 220 as thick as the nano-gap is formed on the substrate 210 using an Atomic Layer Deposition (ALD) process, a hard mask or soft mask is formed on the sacrificial layer 220, the sacrificial layer is etched using the mask pattern as an etch-stop layer, and the mask pattern is then removed. The sacrificial layer pattern 220 formed in this process functions to support the gate 230.

Referring to 200b of FIG. 2, a gate 230 is formed on the sacrificial layer 220. The gate 230 may be made of metal such as, preferably, gold (Au), or polysilicon. Alternatively, the gate 230 may be made of a material, which can be used to form a gate in a typical MOSFET. Since the gate 230 has one end connected to the substrate 210, it is supported although the sacrificial layer 220 is removed as described above.

Referring to 200c and 200d of FIG. 2, the gate layer is patterned. A hard mask 240 to define a gate region is stacked on the gate. The gate layer is partially etched using the hard mask (240) pattern as a mask, and the hard mask (240) pattern is then removed.

Referring to 200e of FIG. 2, the sacrificial layer 220 formed on the substrate 210 is all removed, so that an air gap is formed in a region between the gate 230 and the substrate 210, from which the sacrificial layer 220 has been removed.

Referring to 200f of FIG. 2, a dielectric layer 250 comprising biomolecules is formed in the air gap formed through the removal of the sacrificial layer 220. That is, the receptor biomolecules are fixed to the gate 230 or the substrate 210 using a linker. The linker may employ a SAM. The receptor biomolecules may be selected properly according to the type of detection target materials, and may comprise one of DNA, RNA, nucleotide analogs, protein, peptide, amino acid, ligand, antibody-antigen material, a sugar structure, an organic/inorganic compound, vitamin, drug, enzyme, and so on.

The thickness of the dielectric layer 250 can be controlled easily by controlling the thickness of the sacrificial layer 220 formed through the above process. Further, if the gate 230 is formed to have a shape similar to a bridge as described above, the sacrificial layer 220 between the gate layer 230 and the substrate 210 can be removed easily because the lateral sides of the region between the gate 230 and the substrate 210 are opened. Moreover, a biomolecule material of a fluid state can be easily introduced to the region from which the sacrificial layer 220 has been removed and then fixed thereto.

Figure 3:
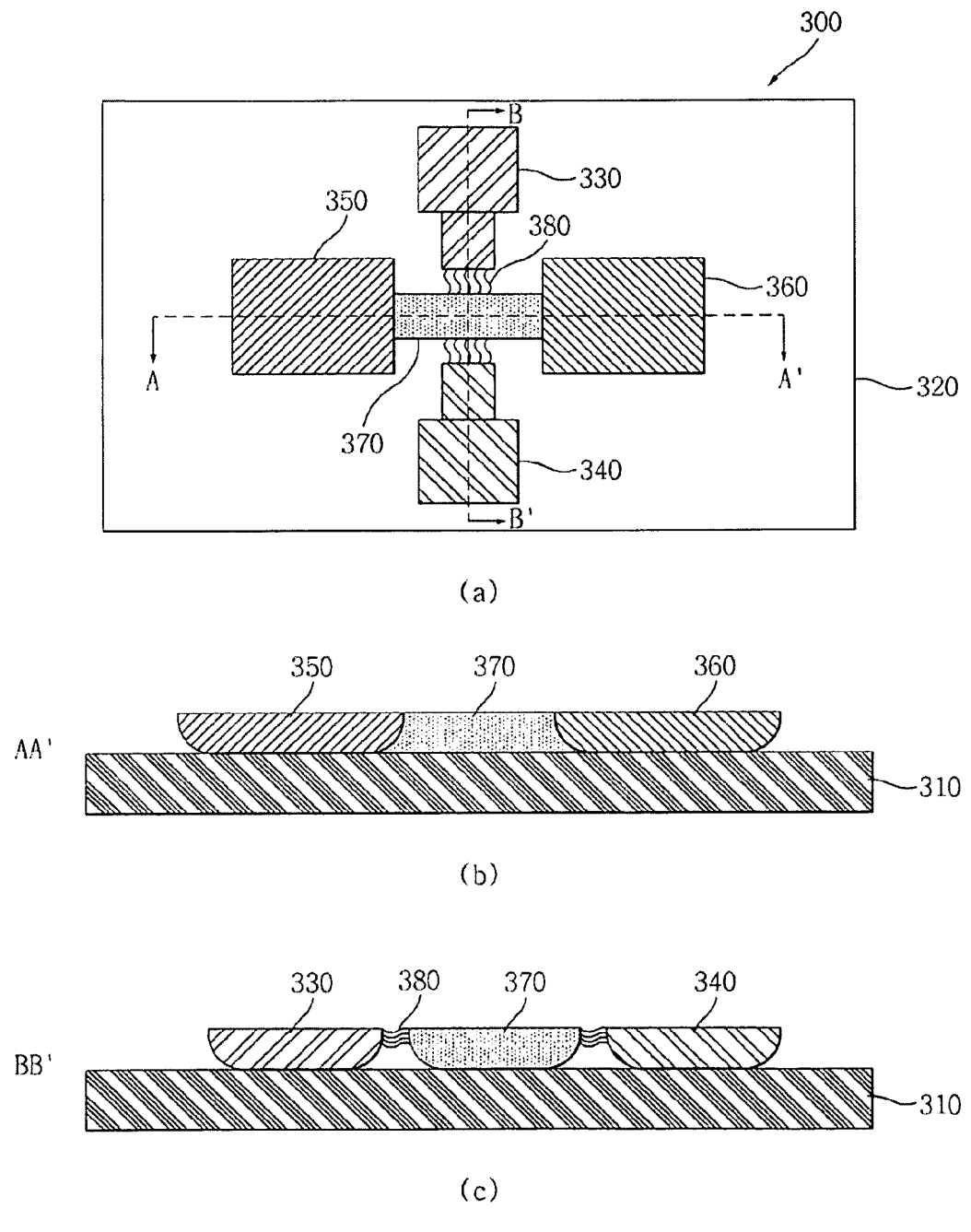
FIG. 3 is a view illustrating a DMFET according to another embodiment of the present invention.

In FIG. 3, (a) is a plan view illustrating a DMFET 300 according to another embodiment of the present invention, (b) is a sectional view of the DMFET taken along line A-A' in (a), and (c) is a sectional view of the DMFET taken along line B-B' in (a).

As shown in FIG. 3, the DMFET 300 comprises a wafer 310, a source 350 and a drain 360 formed on the wafer with them being spaced apart from each other, a channel portion 370 connecting the source 350 and the drain 360, gates 330 and 340 formed on the wafer 310 with them being spaced apart from the channel portion 370, and a dielectric layer 380, which comprises biomolecules and is formed between the channel portion 370 and the gates 330 and 340. The dielectric layer 380 refers to a region, between the gates 330 and 340 and the channel portion 370, comprising receptor biomolecules and a linker for fixing the receptor biomolecules to the gates 330 and 340 and is formed. The linker is comprised of a SAM that can be combined with a gate surface and functions to allow a receptor to be easily connected to the gate surface. The receptor biomolecules may be formed from one of DNA, RNA, nucleotide analogs, protein, peptide, amino acid, ligand, antibody-antigen material, a sugar structure, an organic/inorganic compound, vitamin, drug, enzyme, etc., but may be formed from other materials according to target materials to be detected.

The two gates 330 and 340 are opposite to each other on the basis of the channel portion 370. A double gate type having the two gates 330 and 340 has been described as an example, but the number of the gates is not limited to two. The gates 330 and 340, the source 350, the drain 360, and the channel portion 370 are formed by doping a n-type or p-type impurity into the substrate 320, which is thinly formed on a bulk silicon wafer or a Silicon-On-Insulator (SOI) wafer. It is to be noted that a specific implantation dose and energy can be selected depending on the requirements of a specific end device. The substrate 320 may comprise a silicon substrate.

The gap between the gates 330 and 340 and the channel portion 370 is nanometer in size. The nano-size may be in the range of approximately 10 to 1000 angstrom. The gap may be decided through an e-beam lithography process or a similar process. The dielectric layer 380, which is formed between the gates 330 and 340 and the channel portion 370 and comprises the biomolecules, is fixed to the channel portion 370, the substrate 320 or the gates 330 and 340 using a SAM or through a similar process.

The substrate 320 and the gates 330 and 340 may comprise other semiconductor materials such as germanium (Ge), or other metal materials such as gold (Au). An oxide film is formed on the substrate 320, a polysilicon or poly-germanium thin film is formed using a Chemical Vapor Deposition (CVD) method, and the source 350, the drain 360, the gates 330 and 340, etc. are then formed in the same manner as the SOI wafer process. In this case, the channel region is not excellent in the current property, mobility, and the gain property since it has not a single crystal structure as in the bulk silicon wafer or the SOI wafer, but an amorphous or polycrystalline structure, but is advantageous in that it can form a cheap substrate in the application fields of a sensor.

Referring to FIG. 3(b), the source 350, the channel portion 370, and the drain 360 are formed on the substrate 310. Referring to FIG. 3(c), the two gates 330 and 340, which are opposite to each other with the channel portion 370 intervened therebetween, are formed with them being spaced apart from the channel portion 370. The nano-gap having a nano-size width is formed between the gates 330 and 340 and the channel portion 370. The dielectric layer 380 comprising the biomolecules is formed in the nano-gap. If voltage applied to the gates 330 and 340 forms an electric field, the formed electric field forms a depletion layer in the channel region through the dielectric layer 380. The depletion layer formed as described above hinders a channel from being formed. The formation is dependent on whether the depletion layer exists. This operation principle is very similar to that of a Junction Field Effect Transistor (JFET).

Figure 4:
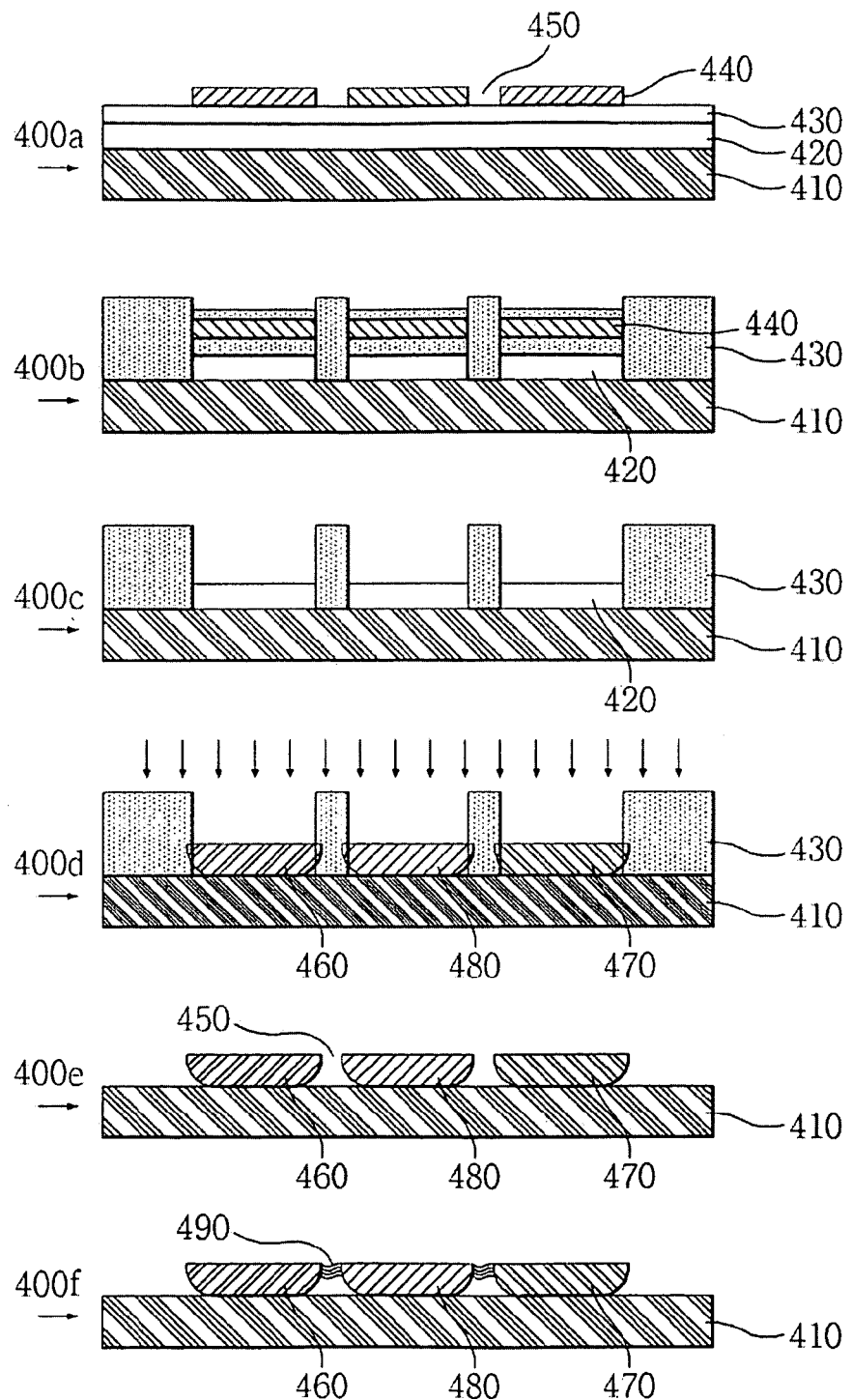
FIG. 4 is a sectional view sequentially illustrating a method of fabricating a DMFET according to another embodiment of the present invention.

FIG. 4 is a sectional view sequentially illustrating a method of fabricating a DMFET according to another embodiment of the present invention. In a method of forming a nano-gap according to an embodiment of the present invention, a substrate and a first insulating layer are sequentially formed on a wafer. A second insulating layer is patterned on a region in which a gate and a channel portion will be formed in the first insulating layer. A constituent material of the first insulating layer is further formed on the first insulating layer using a thermal oxidization method in order to grow the first insulating layer. The first and second insulating layers are etched until the substrate is exposed. An impurity is implanted into the exposed region of the substrate in order to form the gate and the channel portion. The first insulating layer is then etched. A dielectric layer comprising biomolecules is formed between the formed gate and the formed channel portion. Each of the above processes is described in detail with reference to FIG. 4.

Referring to 400a of FIG. 4, a substrate 420 and a first insulating layer 430 are sequentially formed over a wafer 410. The wafer 410 may be a SOT wafer or a bulk-silicon wafer, and the substrate 420 may be a silicon substrate. Second insulating layers 440 are patterned on the first insulating layer 430. At this time, the second insulating layer 440 is patterned so that regions in which gates 460 and 470 and a channel portion 480 will be formed finally are defined, and gaps 450 between the second insulating layer (440) patterns are patterned to have a nano-size. To pattern the second insulting layer(440), a hard mask may be formed on the second insulating layer 440, thus defining the regions in which the gates and the channel portion will be formed, and then the second insulating layers 440 may be patterned using the hard mask pattern as a mask. The first insulating layer 430 may be made of silicon-oxide, and the second insulating layers 440 may be made of silicon-nitride.

Referring to 400b of FIG. 4, the same material as that constituting the first insulating layer 430 is further formed on the first insulating layer 430 using a thermal oxidization method, thus growing the first insulating layer 430. At this time, the material constituting the first insulating layer 430 may also be formed on the second insulating layers 440. If the first insulating layer is grown using the thermal oxidization method as described above, the silicon substrate 420 below the first insulating layer 430 is also oxidized and is thus changed to the same material as that of the first insulating layer 430. In the thermal oxidization process, the plurality of second insulating layers 440 serve as a mask, so that the first insulating layer 430 below the second insulating layers 440 is not thermally oxidized. Accordingly, the silicon substrate 420 can be divided into several isolated elements.

Referring to 400c of FIG. 4, the second insulating layers 440, and the first insulating layer 430 below the second insulating layers 440 are sequentially etched so that the silicon substrate 420 is exposed. At this time, when a material constituting the first insulating layer 430 is stacked on the second insulating layers 440, the material is first etched. Further, the first insulating layer 430 is also etched to a certain extent even in the regions in which the second insulating layers 440 are not formed, but only the first insulating layer 430 is thickly formed, in such regions, the first insulating layer 430 remains to some degree even when the silicon substrate 420 is exposed, and thus serves as a mask in a subsequent process of implanting an impurity into the silicon substrate 420.

Referring to 400d of FIG. 4, an impurity is implanted into the silicon substrate 420 using the remaining first insulating layer 430 as a mask and then activated, thus forming the gates 460 and 470 and the channel portion 480.

Referring to 400e of FIG. 4, the first insulating layer 430 formed on the silicon substrate 420 is all etched. Accordingly, nano-gaps 450 are formed between the gates 460 and 470 and the channel portion 480. A depth of the nano-gap 450 is identical to a thickness of the initial substrate 420, and a width of the nano-gap 450 is decided according to a gap between the second insulating layers 440. The width of the nano-gap 450 may have a nano-size in the range of approximately 10 to 1000 angstrom.

Referring to 400f of FIG. 4, a dielectric layer 490 comprising biomolecules is formed in the nano-gaps 450. In other words, the receptor biomolecules are fixed to the gates 460 and 470 or the channel 480 using a linker. A SAM may be used as the linker. The receptor biomolecules may be selected appropriately according to the type of detection target materials, and may comprise one of DNA, RNA, nucleotide analogs, protein, peptide, amino acid, ligand, antibody-antigen material, a sugar structure, an organic/inorganic compound, vitamin, drug, enzyme, and so on.

Figure 5:
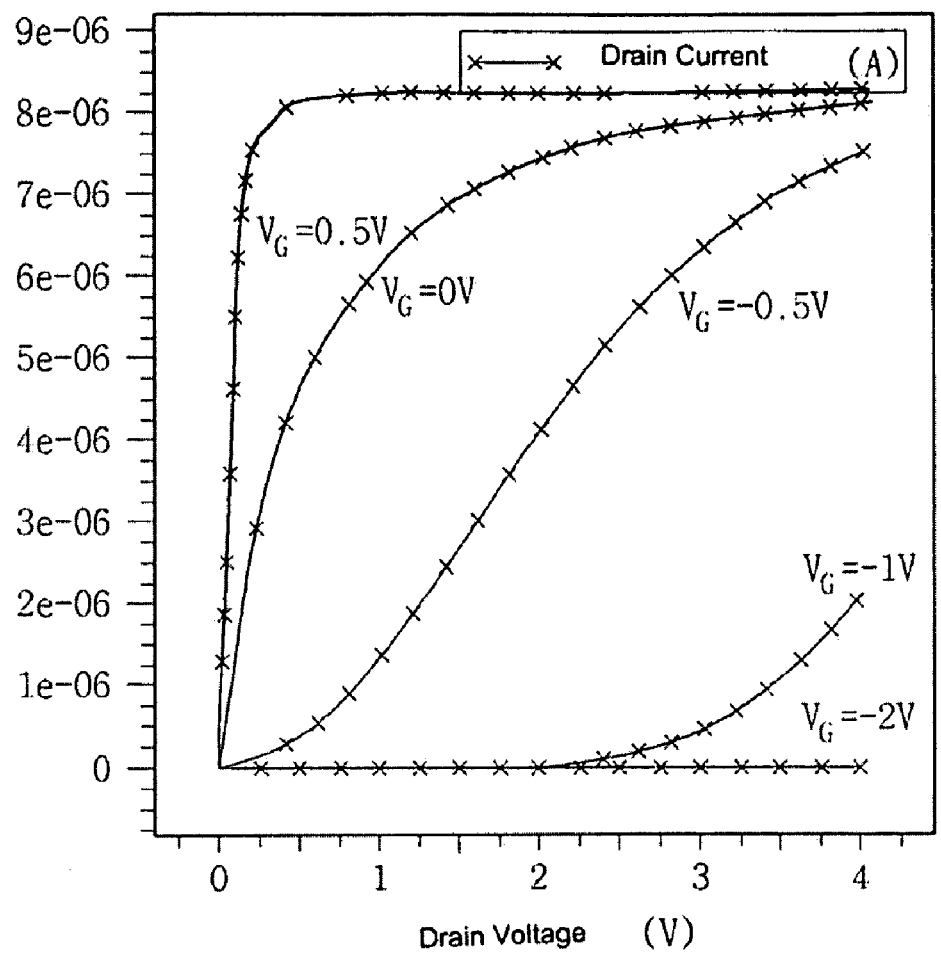
FIG. 5 is a graph showing a simulation result of drain currents according to gate voltages in the DMFET shown in FIG. 3 according to another embodiment of the present invention.

FIG. 5 is a graph showing a simulation result of drain currents according to gate voltages in the DMFET shown in FIG. 3 according to another embodiment of the present invention. In the present simulation, ATLAS simulator of Silvaco Data Systems Inc. was used. In the present simulation, the length of the channel portion 370 was 300 rim and the width of the nano-gap was 40 nm. All the gates 350 and 360 and the channel portion 370 were doped to be an n-type and the doping concentration was $5\times0^{15}$. If $5\times0^{15}$. If voltage is applied to the gates 350 and 360, an electric field is formed through the dielectric layer 380. A depletion layer is formed in the channel portion 370 by means of the electric field. If the gate voltage exceeds a certain range, the depletion layer formed in the channel portion 370 by means of the gate voltage prevents the flow of electrons in the channel portion 370, thus deciding the flow of current between the source 350 and the drain 360. It can be said that this electrical operation property of the device is similar to that of the JFET. Current values flowing between the source 350 and the drain 360 when the voltage applied to the gates 350 and 360 is changed to −2V, −1, −0.5V, 0V or 0.5V are shown FIG. 5. From FIG. 5, it can be seen that when the voltage applied to the gates 350 and 360 exceeds −2V, current flows through the source 350 and the drain 360.

Figure 6:
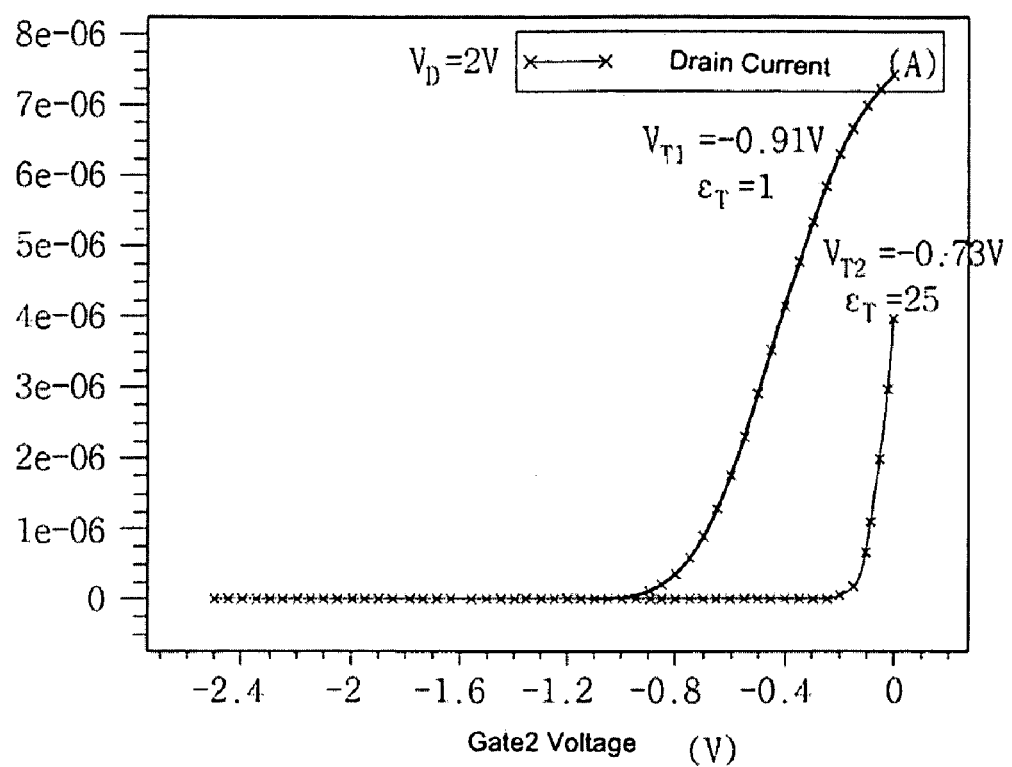
FIG. 6 is a graph showing a simulation result of threshold voltages according to the type of a dielectric material in the DMFET shown in FIG. 3 according to another embodiment of the present invention.

FIG. 6 is a graph showing a simulation result of threshold voltages according to the type of a dielectric material in the DMFET shown in FIG. 3 according to another embodiment of the present invention. FIG. 6 is a graph showing a difference in the threshold voltage when the dielectric layer 380 is (1) in an air gap state (the air is introduced to the nano-gap) ($\epsilon_r=1$) and (2) comprises biomolecules ($\epsilon_r=25$) in the DMFET shown in FIG. 3 according to another embodiment of the present invention. The amount of the electric field formed by the gate voltage is varied according to a material forming the dielectric layer 380, which makes different the thickness of the depletion layer formed in the channel portion 370. Due to this difference, there occurs a difference in the gate voltage, which prevents the flow of current between the source 350 and the drain 360 when compared with the air gap device. This difference is varied according to which molecules are filled in the nano gap between the gate and the channel portion.

Figure 7:
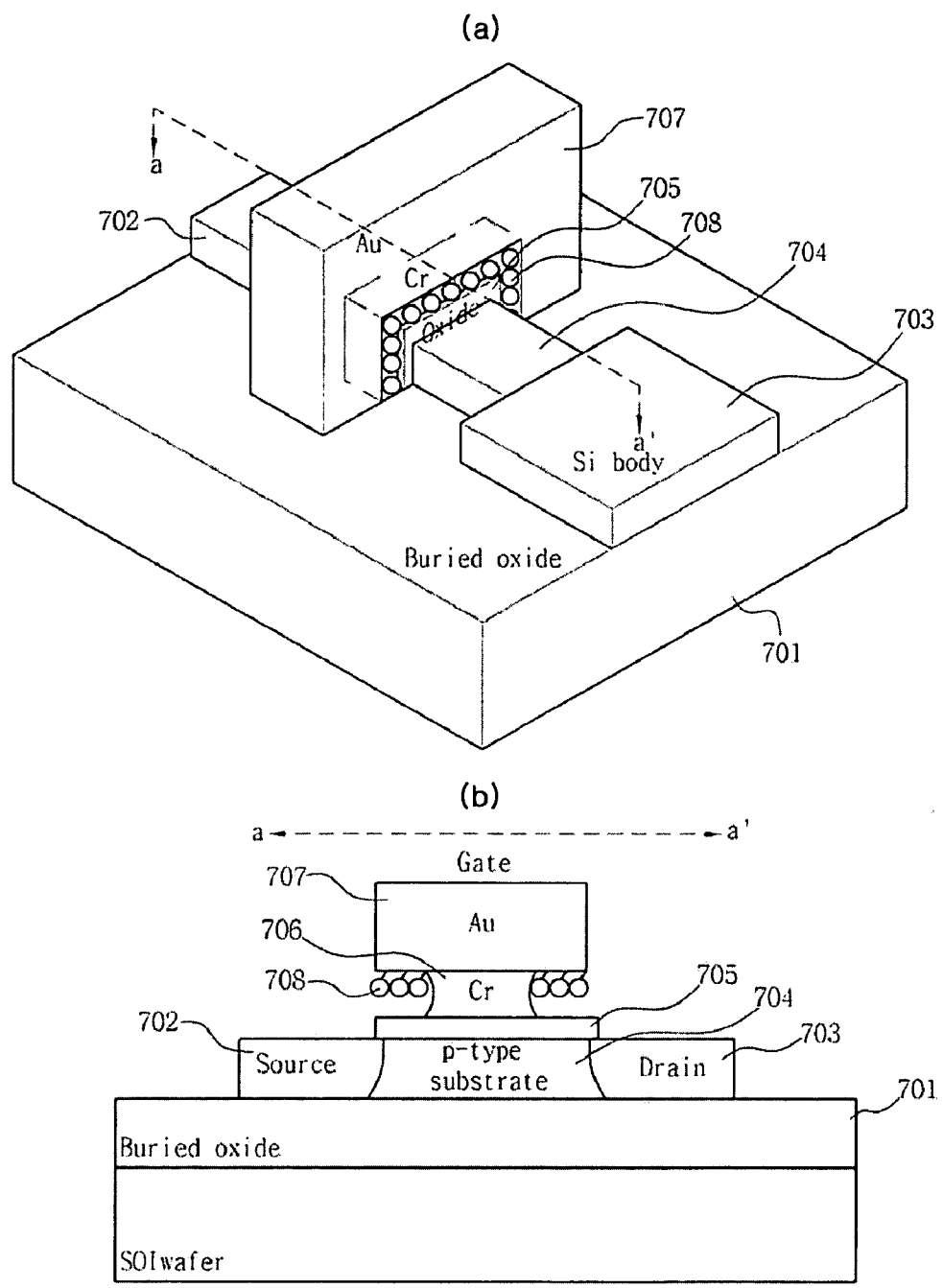
FIG. 7 is a perspective view illustrating a DMFET according to still another embodiment of the present invention.

FIG. 7 is a serspective view sequentially illustrating a method of fabricating a DMFET according to still another embodiment of the present invention. The DMFET shown in FIG. 7 can be fabricated using the conventional Complementary Metal Oxide (CMOS) semiconductor process in the same manner as the above-described DMFET. Referring to FIG. 7, a source 702, a channel portion 704, and a drain 703 are formed over a SOI substrate 701 into which a P type impurity has been implanted. A gate 707 is formed over the channel portion 704. The gate 707 is spaced apart from and opposite to the channel portion 704. A sacrificial layer 706 may be formed between the channel portion 704 and the gate 707. As an embodiment, the sacrificial layer 706 may be made of chrome (Cr). Both ends of the sacrificial layer 706 are etched, thus forming a nano-sized air gap between the channel portion 704 and the gate 707. A depth of a horizontal direction of the air gap may be decided according to the extent that both ends of the sacrificial layer 706 are etched. Alternatively, the sacrificial layer 706 may be fully etched and removed. A linker is formed at the bottom of the gate 707 exposed by the formed air gap. The linker may be formed from a SAM. When the gate 707 is made of gold (Au), the linker may be formed from a thiol SAM. When the gate 707 is made of silicon, the linker may be formed from a silane SAM. The linker is combined with biomolecules 708 and then fixed thereto. The biomolecules 708 may be formed from one of DNA, RNA, nucleotide analogs, protein, peptide, amino acid, ligand, an antibody-antigen material, a sugar structure, an organic/inorganic compound, vitamin, drug, enzyme, and so on, but not limited therto. The biomolecules may be properly selected according to target materials to be detected. Alternatively, an insulating layer 705 may be formed on the channel portion 704. The insulating layer 705 functions to prevent the gate 707 and the channel portion 704 from being shortened by the biomolecules 708, or the biomolecules 708 and detection target materials combined with the biomolecules 708.

Figure 8:
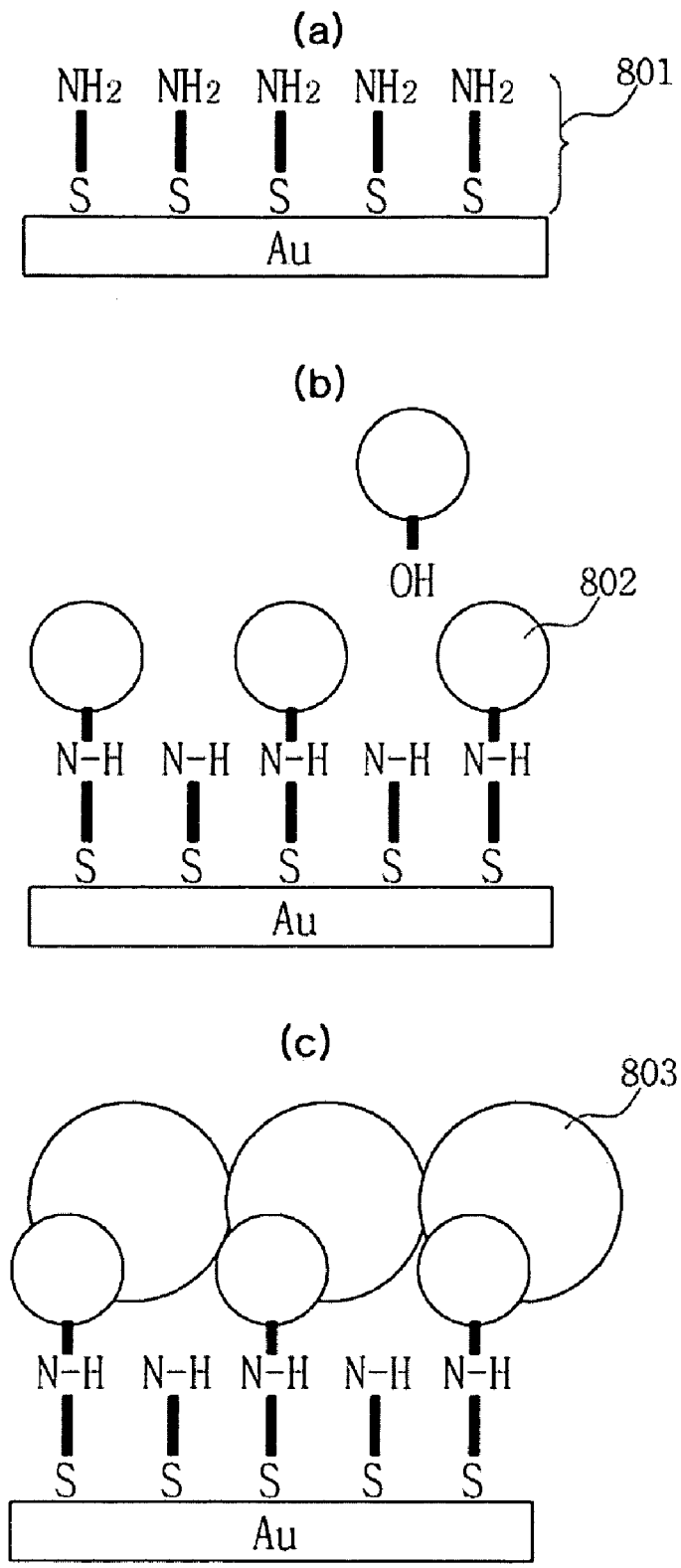
FIG. 8 is a view illustrating an operation of the DMFET according to the present invention.

FIG. 8 is a view illustrating an operation of the DMFET according to the present invention. A SAM 801 is formed on a gate as shown in FIG. 8(a). Biomolecules 802 are fixed to the SAM 801 as shown in FIG. 8(b). Accordingly, as shown in FIG. 8(c), when detection target materials 803 exist in an environment in which a DMFET is placed, the detection target materials 803 are fixed to an air gap of the DMFET through coupling of the detection target materials 803 and the biomolecules 802, so the property of the DMFET is changed.

As described above, in accordance with the structure of the DMFET and the method of fabricating the same according to an embodiment of the present invention, the thickness of the nano-gap can be controlled easily by controlling the thickness of the sacrificial layer. Further, since the gate layer is formed to have a shape similar to a bridge, the sacrificial layer can be removed easily, and biomolecule materials of a fluid state can be easily introduced to a region from which the sacrificial layer has been removed and then fixed thereto. Accordingly, a DMFET having a novel structure of a nano-gap with a high reproducibility can be provided.

In addition, the size of the DMFET can be reduced compared with a conventional biosensor device in which a dielectric layer and a biomaterial exist separately, sensitivity to a variation in the electrical property of a device according to a change of the biomaterial can be increased, and further improved detection of the biomaterial is possible.

In accordance with the structure of the DMFET and the method of fabricating the same according to another embodiment of the present invention, the size of the nano-gap can be controlled easily by means of isolation through a lithography process. Accordingly, a DMFET having a nano-gap with a high reproducibility can be fabricated.

While the invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A method of fabricating a DMFET, comprising the steps of:
   (a) forming a sacrificial layer on a substrate, so that at least a first portion and a second portion of the substrate remain exposed;
   (b) forming a gate layer on the sacrificial layer and the first and second exposed portions of the substrate, the gate layer forming a bridge that extends from the first exposed portion to the second exposed potion and over a portion of the sacrificial layer which is located between the first and second exposed portions;
   (c) removing the portion of the sacrificial layer so that a gap is formed between the bridge of the gate layer and the substrate; and
   (d) forming a dielectric layer, comprising biomolecules, in the gap.

2. The method of claim 1 wherein step (d) comprises forming the dielectric layer by fixing receptor biomolecules to the gate layer or to the substrate in the gap, the receptor biomolecules contributing to an overall dielectric constant of the dielectric layer, and further changing the overall dielectric constant when combined with target materials being detected.

3. The method of claim 1, further comprising the step of patterning the gate layer between the step (b) and the step (c).

4. The method of claim 1, wherein the sacrificial layer comprises at least one of metal oxide such as silicon oxide, Al2O3 or HfO2, metal such as Cr, Ti or Al, an organic layer such as a Self-Assembled Monolayer (SAM), and a photoresist.

5. A method of fabricating a DMFET, the method comprising:
   (a) forming a patterned sacrificial layer on a substrate such that a portion of the substrate remains exposed;
   (b) forming a gate layer on the substrate and the sacrificial layer such that the gate layer comes in contact with the exposed portion of the substrate;
   (c) removing the sacrificial layer; and
   (d) forming a dielectric layer by fixing receptor biomolecules to the gate layer or to the substrate in a space formed by removing the sacrificial layer, the receptor biomolecules contributing to an overall dielectric constant of the dielectric layer, and further changing the overall dielectric constant when combined with target materials being detected.

6. The method of claim 5, further comprising patterning the gate layer between the step (b) and the step (c).

7. The method of claim 5, wherein the sacrificial layer comprises at least one of metal oxide such as silicon oxide, Al2O3 or HfO2, metal such as Cr, Ti or Al, an organic layer such as a Self-Assembled Monolayer (SAM), and a photoresist.

8. The method of claim 5, wherein in the step (d), the dielectric layer is formed using a SAM or a dehydration and condensation reaction.

9. A method of fabricating a DMFET, comprising:
(a) forming a substrate on a wafer and forming a first insulating layer on the substrate;
(b) patterning a second insulating layer on the first insulating layer so that portions of the first insulating layer remain exposed;
(c) subjecting the exposed portions of the first insulating layer to a thermal oxidation process so that portions of the substrate below the exposed portions of the first insulating layer are converted to a constituent material of the first insulating material;
(d) etching the second insulating layer and portions of the first insulating layer located below the second insulating layer until portions of the substrate below the second insulating layer are exposed, wherein portions of the first insulating layer not located below the second insulating layer remain on the wafer and act as a mask;
(e) forming at least two gates and a channel portion by implanting an impurity into the exposed portions of the substrate;
(f) etching the remaining portions of the first insulating layer so that gaps are formed between the gates and the channel portion; and
(g) forming a dielectric layer comprising biomolecules in each of the gaps between the gates and the channel portion.

10. A method of fabricating a DMFET, the method comprising:
(a) forming a substrate on a wafer and forming a first insulating layer on the substrate;
(b) forming a second insulating layer on the first insulating layer and patterning the second insulating layer such that portions of the first insulating layer remain exposed;
(c) converting the substrate's portion corresponding to the exposed portions of the first insulating layer into the same material as the first insulating layer through a thermal oxidation process; (d) etching the first and second insulating layers until the substrate's portions corresponding to the second insulating layer are exposed, wherein portions of the first insulating layer not located below the second insulating layer remain on the wafer and act as a mask;
(e) forming at least two gates and a channel portion by implanting an impurity into the exposed substrate;
(f) etching the first insulating layer so that gaps are formed between the gates and the channel portion; and
(g) forming a dielectric layer in the gaps between the gates and the channel portion, the dielectric layer comprising biomolecules.

11. The method of claim 10, wherein:
the first insulating layer comprises silicon-oxide, and
the second insulating layer comprises silicon-nitride.

12. The method of claim 10, wherein in the step (g), the dielectric layer is formed using a SAM or dehydration and condensation reaction.

13. The method of claim 10 wherein step (g) comprises forming the dielectric layer by fixing receptor biomolecules to the gates, to the channel portion, or to the wafer, the receptor biomolecules contributing to an overall dielectric constant of the dielectric layer, and further changing the overall dielectric constant when combined with target materials being detected.

* * * * *